United States Patent
Tamada et al.

(10) Patent No.: US 9,440,005 B2
(45) Date of Patent: Sep. 13, 2016

(54) SUBSTRATE FOR FEEDING CELLS AND/OR TISSUES, CELL/TISSUE-FEEDER AND METHOD FOR THE PRODUCTION OF THE SAME, METHOD FOR THE REGENERATION OF TISSUES, AND METHOD FOR THE PRODUCTION OF POROUS BODIES

(75) Inventors: Yasushi Tamada, Ibaraki (JP); Katsura Kojima, Ibaraki (JP); Naohide Tomita, Kyoto (JP); Eiichi Hirakata, Kyoto (JP)

(73) Assignees: National Institute of Agrobiological Sciences, Ibaraki (JP); Kyoto University, Kyoto (JP)

( * ) Notice: Subject to any disclaimer, the term of this patent is extended or adjusted under 35 U.S.C. 154(b) by 70 days.

(21) Appl. No.: 13/391,551

(22) PCT Filed: Aug. 23, 2010

(86) PCT No.: PCT/JP2010/064193
§ 371 (c)(1), (2), (4) Date: Feb. 21, 2012

(87) PCT Pub. No.: WO2011/021712
PCT Pub. Date: Feb. 24, 2011

(65) Prior Publication Data
US 2012/0148639 A1    Jun. 14, 2012

(30) Foreign Application Priority Data
Aug. 21, 2009 (JP) ................................. 2009-192600

(51) Int. Cl.
| C12N 5/00 | (2006.01) |
| C12N 5/02 | (2006.01) |
| A61L 27/56 | (2006.01) |
| A61L 27/22 | (2006.01) |
| A61L 27/38 | (2006.01) |

(52) U.S. Cl.
CPC ............. *A61L 27/56* (2013.01); *A61L 27/227* (2013.01); *A61L 27/3804* (2013.01)

(58) Field of Classification Search
None
See application file for complete search history.

(56) References Cited

U.S. PATENT DOCUMENTS

| 3,574,150 | A * | 4/1971 | Jefferson et al. ................. 1/63 |
| 6,303,136 | B1* | 10/2001 | Li et al. ......................... 424/424 |
| 6,540,780 | B1* | 4/2003 | Zilla et al. ..................... 623/1.39 |
| 6,554,857 | B1* | 4/2003 | Zilla et al. ..................... 623/1.23 |
| 6,627,422 | B1* | 9/2003 | Li et al. ......................... 435/182 |
| 6,673,108 | B2* | 1/2004 | Zilla et al. ....................... 623/1.4 |
| 2002/0151968 | A1* | 10/2002 | Zilla et al. ..................... 623/1.39 |
| 2002/0169499 | A1* | 11/2002 | Zilla et al. ..................... 623/1.15 |
| 2005/0142162 | A1* | 6/2005 | Hunter et al. .................. 424/423 |
| 2005/0142163 | A1* | 6/2005 | Hunter et al. .................. 424/423 |
| 2005/0148512 | A1* | 7/2005 | Hunter et al. .................... 514/12 |
| 2005/0260706 | A1* | 11/2005 | Kaplan et al. ................. 435/69.1 |
| 2006/0015053 | A1* | 1/2006 | Crisp ............................... 602/43 |
| 2006/0121080 | A1* | 6/2006 | Lye et al. ....................... 424/423 |
| 2006/0129234 | A1* | 6/2006 | Phaneuf et al. ............... 623/1.54 |
| 2006/0147492 | A1* | 7/2006 | Hunter et al. .................. 424/426 |
| 2006/0149358 | A1* | 7/2006 | Zilla et al. ..................... 623/1.22 |
| 2006/0193886 | A1* | 8/2006 | Owens et al. .................. 424/423 |
| 2006/0193887 | A1* | 8/2006 | Owens et al. .................. 424/423 |
| 2006/0193888 | A1* | 8/2006 | Lye et al. ....................... 424/423 |
| 2006/0193889 | A1* | 8/2006 | Spradlin et al. ............... 424/423 |
| 2006/0193890 | A1* | 8/2006 | Owens et al. .................. 424/423 |
| 2006/0205927 | A1* | 9/2006 | Jin et al. ......................... 530/353 |
| 2006/0276878 | A1* | 12/2006 | Owens et al. .................. 623/1.15 |
| 2006/0276885 | A1* | 12/2006 | Lye et al. ....................... 623/1.39 |
| 2007/0187862 | A1* | 8/2007 | Kaplan et al. ............. 264/172.11 |
| 2008/0033522 | A1* | 2/2008 | Grewe et al. .................. 623/1.11 |
| 2008/0086198 | A1* | 4/2008 | Owens et al. .................. 623/1.39 |
| 2008/0243096 | A1* | 10/2008 | Svedman ........................ 604/305 |
| 2009/0093778 | A1* | 4/2009 | Svedman ........................ 604/290 |
| 2009/0202614 | A1* | 8/2009 | Kaplan et al. ................. 424/443 |
| 2009/0234026 | A1* | 9/2009 | Kaplan et al. ................. 514/773 |
| 2010/0055438 | A1* | 3/2010 | Kaplan et al. ................. 428/221 |
| 2011/0020409 | A1* | 1/2011 | Altman et al. ................. 424/400 |
| 2011/0066242 | A1* | 3/2011 | Lu et al. ...................... 623/13.14 |
| 2013/0190222 | A1* | 7/2013 | Kaplan et al. ................... 514/1.1 |

FOREIGN PATENT DOCUMENTS

| CN | 101474430 | * | 1/2009 | ............. A61L 27/48 |
| CN | 101474430 A | | 7/2009 | |
| CN | 101502669 A | | 8/2009 | |
| JP | 2002-186847 A | | 7/2002 | |

(Continued)

OTHER PUBLICATIONS

Kim et al., Biomater., 26:4442-4452 2005).*

(Continued)

*Primary Examiner* — Blaine Lankford
*Assistant Examiner* — Thomas J Visone
(74) *Attorney, Agent, or Firm* — Arent Fox LLP (57) ABSTRACT

A substrate for feeding cells and/or tissues which is composed of a porous body having a thin film surface and a porous surface and which can be used in the regenerative medical techniques. A cell/tissue feeder is produced by cultivating tissues on the porous surface of the porous body. Cells are seeded on the porous surface of the body, followed by the cultivation of the cells to thus form and/or regenerate tissues. An aqueous solution of silk proteins, to which a water-soluble organic solvent is added, is introduced into a mold whose bottom or top surface is surface-roughened, followed by freezing the aqueous solution and then thawing the frozen aqueous solution to form a porous body having a thin film surface and a porous surface.

28 Claims, 6 Drawing Sheets
(5 of 6 Drawing Sheet(s) Filed in Color)

(56) References Cited

FOREIGN PATENT DOCUMENTS

| | | | |
|---|---|---|---|
| JP | 2003-038170 A | 2/2003 | |
| JP | 2004-267777 A | 9/2004 | |
| JP | 2006-230874 A | 9/2006 | |
| JP | 2007-229124 A | 9/2007 | |
| JP | 2008-194301 A | 8/2008 | |
| WO | WO 03/011343 A1 | 2/2003 | |
| WO | WO 2010/081408 * | 7/2010 | ............ A61L 27/22 |

OTHER PUBLICATIONS

MacIntosh et al., J. Tissue Eng. Regen. Med., 2:71-80 (2008).*
Hideyuki Aoki, et al., "Culture of Chondrocytes in Firbroin-Hydrogel Sponge", Bio-Medical Materials and Engineering, 2003, pp. 309-316, vol. 13, IOS Press.
Shinichi Terada et al., Experimental Discussion of Cartilage Regeneration of Silk Fibroin Scaffolding, The $9^{th}$ Annual Meeting of the Japanese Societies for Tissue Engineering, 2008, p. 10, Abstract No. OA3-3.

* cited by examiner

Silk sponge fixed to a joint through suture

SUBSTRATE FOR FEEDING CELLS AND/OR TISSUES, CELL/TISSUE-FEEDER AND METHOD FOR THE PRODUCTION OF THE SAME, METHOD FOR THE REGENERATION OF TISSUES, AND METHOD FOR THE PRODUCTION OF POROUS BODIES

CROSS-REFERENCED TO RELATED APPLICATION

This application is a National Stage entry of International Application No. PCT/JP2010/064193, filed Aug. 23, 2010, which claims priority to Japanese Patent Application No. 2009-192600, filed Aug. 21, 2009, the disclosure of the prior applications are incorporated in their entirety by reference.

TECHNICAL FIELD

The present invention relates to a substrate for feeding cells and/or tissues (hereinafter referred to as "cells/tissues" or cell/tissue in the specification and claims, as needed), a cell/tissue feeder and a method for the production of the same, a method for the regeneration of tissues, as well as a method for the production of a porous body.

BACKGROUND ART

Because of the recent considerable advance in the medical technology, it has been recognized that the regeneration medical treatment including, for instance, the organ transplantation is important as a next-generation medical treatment for the purpose of treating the tissues, organs and/or parts or systems, which lose their shapes and/or functions. For example, there has been attempted cell transplantation while making use of a variety of stem cells as a therapy which can take the place of the heart transplant for the heart undergoing dysfunction, which suffers from a problem of the lack of donors.

There has recently been tried a tissue transplantation technique in which a three-dimensional myocardial tissue is, for instance, constructed in vitro and then the resulting three-dimensional myocardial tissue is transplanted into a patient. For instance, it has been known to produce various kinds of cell sheets and three-dimensional structures (see, for instance, Patent Document 1 specified below).

It has been believed that the key points of the regenerative medical techniques are the following three elements: cells, scaffolding materials for cells and humoral factors such as growth factors. Practically used as such scaffolding materials are three-dimensional porous bodies (sponge) mainly composed of collagen and poly(lactic acids) (see, for instance, Patent Document 2 specified below). There has been reported an example in which cartilage or the like can be regenerated through the use of these materials, but this technique suffers from such a problem that the technique can be applied only to injuries each extending over a small region. This is because such a technique cannot supply a large quantity of cells to the injured site although a large quantity of cells should be supplied thereto at the initial stage of the regeneration thereof; the materials cannot be sutured and cannot likewise satisfactorily be fixed to the damaged sites; and the materials do not have satisfactory compatibility, in particular, in the mechanical characteristics such as strength and elastic modulus.

On the other hand, there has been reported, as novel scaffolding materials, porous bodies mainly composed of silk proteins. However, the conventional porous bodies composed of silk proteins are produced according to a known manufacturing process mainly comprising the step of lyophilization and accordingly, the resulting porous bodies do not have satisfactory mechanical characteristics such as strength and elastic modulus and, for this reason, the applications thereof are quite limited as well. Contrary to this, there has also been known a method for the production of a hydrogel which shows sufficient mechanical strength (see, for instance, Patent Document 3 specified below). In this respect, it has been found that cells can undergo proliferation while they hold their differentiated states, within the hydrogels produced according to this technique, and it has been confirmed that a satisfactorily regenerated tissue is formed even at a very small number of initially inoculated or seeded cells (see, for instance, Non-patent Document 1 specified below). Accordingly, the hydrogel disclosed in Patent Document 3 may serve as an excellent scaffold material for the regeneration of a tissue, which has never been known formerly. However, these materials are not bio-absorbable ones unlike collagen or the like, while they are biodegradable ones and therefore, the applications of such a material has presently been limited even in the fields of, for instance, the regenerative medical techniques.

Moreover, when considering the more practical and clinical use of such a material, it would be desirable to achieve an effect of protecting the surface of an injured site during the term of the repair and regeneration of the damaged tissues; the secure suture and fixation of the material to the injured site; and the reduction of any mechanical load possibly applied to the injured site and it would likewise be desirable that the material makes it possible to regenerate tissues even when the damage thereof is severe and wide and the damaged sites lose a large number of normal cells and tissues. In addition, it is also desirable to protect the tissues opposite to the surface of injured sites during the term required for the repair and regeneration of the damaged tissues. However, there has not yet been developed presently any substrate (scaffolding materials) for supporting cells/tissues, which shows such an excellent function.

PRIOR ART LITERATURE

Patent Document

[Patent Document 1] Japanese Un-Examined Patent Publication No. 2003-38170;
[Patent Document 2] International Un-Examined Patent Publication No. 2003/011343 Pamphlet;
[Patent Document 3] Japanese Patent No. 3,412,014.

No-Patent Document

[No-Patent Document 1] T. Aoki et al., Biomed. Mater. Eng., 2003, 13: 309.

DISCLOSURE OF THE INVENTION

Problems that the Invention is to Solve

It is an object of the present invention to solve the foregoing problems associated with the conventional techniques and more specifically to provide a substrate for feeding cells and/or tissues and a cell/tissue feeder, which can be used in the regenerative medical techniques, and a method for the production of the same, a method for the regeneration of tissues, as well as a method for the production of a porous body, wherein these materials can provide a large quantity of cells; they permit the secure suture of these materials and the secure fixation thereof to the injured site; they can reduce any mechanical load possibly applied to the surface of injured sites; they have an effect of protecting the surface of injured regions and the surface of the regions opposed to the injured ones during the term required for the repair and regeneration of the damaged tissues; and they further make it possible to regenerate tissues even when the damage thereof is severe and wide and the damaged sites lose a large number of normal cells and tissues.

The inventors of this invention have exerted all possible efforts to solve the foregoing problems, have found, as a result, that if improving the method for the production of a hydrogel as disclosed in Patent Document 3 and producing a porous body having a thin film surface and a porous surface according to the improved method, the use of the resulting porous body would permits the secure suture thereof and the secure fixation thereof to the injured site; the reduction of any mechanical load possibly applied to the injured sites; the achievement of an effect of protecting the surface of injured region and the surface of the region opposite to the injured region; and the regeneration of tissues over a wide range, and that if inoculating or seeding, in advance, cells into the porous surface of this porous body and cultivating the cells to thus form a tissue, the use of such a porous body carrying the tissues thus formed would permit the considerably excellent tissue-regeneration at a damaged tissue-containing site, and have thus completed the present invention.

Means for the Solution of the Problems

The substrate for feeding cells and/or tissues according to the present invention is characterized in that it is composed of a porous body having a thin film surface and a porous surface. In this respect, the porous surface comprises a porous layer or porous portions and the surface of the porous body may be at least superficially porous or entirely porous.

The substrate for feeding cells/tissues according to the present invention is characterized in that the thin film surface and the porous surface of the porous body consist of a silk protein.

The cell/tissue feeder according to the present invention is characterized in that it is composed of consists of a porous body having a thin film surface and a porous surface and that the porous body comprises cultured cells/tissues on the porous surface thereof.

The cell/tissue feeder according to the present invention is characterized in that the cells are ones selected from the group consisting of cartilage cells, myeloid cells or bone-marrow cells, peripheral mononuclear cells, myeloid mononuclear cells, somatic stem cells, and pluripotent cells.

The cell/tissue feeder according to the present invention is characterized in that the tissues are ones selected from the group consisting of cartilage tissues, skin tissues (such as epidermal tissues and dermal tissues), bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues.

The cell/tissue feeder according to the present invention is characterized in that the cells are cartilage cells and the tissues are cartilage tissues.

The use of the substrate for feeding cells/tissues which consists of such a porous body which simultaneously has a thin film surface and a porous surface and which is thus provided by the present invention, would permit the improvement of the ability of fixing the same to the surface of an injured site; the protection of the surface of an injured site due to the reduction of the mechanical load possibly applied to the surface of the injured site (tissue defective region); the migration of cells towards the target tissue (the migration of cells towards the damaged surface of the tissue) after the cell-proliferation; and the occurrence of excellent tissue regeneration in the proximity to the porous body, and the use of the substrate for feeding cells/tissues would likewise permit the regeneration of tissues even when they are severely and widely damaged and they are greatly deficient in the number of normal cells and tissues.

The method for the production of a cell/tissue feeder according to the present invention is characterized in that it comprises the steps of inoculating seed cells or seeding cells on the porous surface of the foregoing porous body and cultivating the cells to thus form tissues.

In the foregoing method for the production of a cell/tissue feeder, the cells and the tissues are the same as those described above in connection with the cell/tissue feeder.

The method for the regeneration of tissues according to the present invention is characterized in that it comprises the steps of seeding cells on the porous surface of the foregoing porous body and cultivating the cells to thus form tissues.

The foregoing method for the regeneration of tissues is further characterized in that the cells are cultivated to give tissues and then the resulting tissues are adapted to the tissue defective site.

In the foregoing method for the regeneration of tissues, the cells and the tissues are the same as those described above in connection with the cell/tissue feeder.

The method for the production of a porous body according to the present invention is characterized in that it comprises the steps of introducing an aqueous solution of a silk protein, to which a water-soluble organic solvent has been added in an amount ranging from 0.05 to 10% by volume, into a mold having a surface-roughened bottom or top surface; freezing the aqueous solution over a predetermined time period; and then thawing the frozen aqueous solution to thus form a porous body consisting of the silk protein and having a thin film surface and a porous surface. In this respect, if the amount of the water-soluble organic solvent used is less than 0.05% by volume, any desired porous body cannot be formed in some cases, while if it exceeds 10% by volume, the silk protein may undergo precipitation and there is observed such a tendency that the resulting porous body does not have a satisfactory mechanical strength.

The foregoing method for the production of a porous body is characterized in that the surface-roughened surface of the body may be one formed by adhering filter paper, a nonwoven fabric, or a surface-roughened film onto the mold surface, or one formed by mechanically or chemically treating the surface of the mold.

Effects of the Invention

The present invention makes use of a porous body having a thin film surface and a porous surface and accordingly permits the achievement of the following effects:
(1) The fixing ability of the cells and/or tissues is improved due to the presence of the thin film surface;
(2) After cells are cultivated, the resulting cells can travel only towards an intended or target tissue, since the porous body is provided with a thin film surface;
(3) The tissue defective surface is covered with the thin film surface of the body and therefore, the damaged tissue is protected from any mechanical load possibly applied to the damaged surface and the surface opposed thereto and the lubricant characteristics accompanied by the movement thereof can thus be ensured;

(4) When using the cell/tissue feeder according to the present invention, cells migrate from the feeder to the surface of a tissue-deficient site, or excellent tissue-regeneration is initiated in the vicinity of the porous body due to a humoral factor such as a growth factor released from the tissue feeder and accordingly, the cell/tissue feeder may, if necessary, be removed from the host in the future.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5(*a*-2) shows an image of tissues obtained using a substrate made of silk fibroin on which cartilage tissues have been formed, wherein the cartilage tissues are subjected to the Collagen II immunostaining; FIG. 5(*b*-1) shows an image of tissues obtained using simply a substrate made of silk fibroin which is completely free of any cartilage tissue formed thereon, wherein the surface of the patellar joint is subjected to the H.E. staining; and FIG. 5(*b*-2) shows an image of tissues obtained using a substrate made of silk fibroin which is completely free of any cartilage tissue formed thereon, wherein the cartilage tissues are subjected to the Collagen II immunostaining.

FIG. 6(*b*) shows an image of the tissues of the patellar joint observed after 6 weeks from the transplantation of the substrate.

MODE FOR CARRYING OUT THE INVENTION

In an embodiment of the substrate for feeding cells and/or tissues (at least one selected from the group consisting of cells and tissues) according to the present invention, the substrate consists of a porous body composed of a silk protein and having a thin film surface and a porous surface.

According to an embodiment of the cell/tissue feeder, which is herein provided by the present invention, the feeder comprises a porous body composed of a silk protein and having a thin film surface and a porous surface and cells and/or tissues cultivated on the porous surface of the porous body. In the cell/tissue feeder, the cells are preferably cartilage cells and the tissues are preferably cartilage tissues.

According to an embodiment of the method for the production of a cell/tissue feeder used in the regenerative medical techniques, which is herein provided by the present invention, cells can be inoculated on the porous surface of a porous body which is composed of a silk protein and which has a thin film surface and a porous surface and a tissue can be formed on the porous body by the seeding of the cells under the known culture conditions to thus produce a cell/tissue feeder. In this respect, the cells are preferably cartilage cells and the tissues are preferably cartilage tissues.

According to an embodiment of the method for the regeneration of tissues used in the regenerative medical techniques, which is herein provided by the present invention, cartilage cells or cartilage cell aggregates, each of which contains a plurality of cartilage cells associated with one another, can be seeded or inoculated on the porous surface of a porous body which is composed of a silk protein and has a thin film surface and a porous surface, and then the cells or cell aggregates can be cultivated under the known culture conditions to thus form regenerated tissues. In this case, the seeding or inoculation and cultivation of the cells or tissues can be carried out in vitro. Moreover, the resulting tissues can be adapted to a tissue defective site or region.

Examples of the foregoing cells include ones selected from the group consisting of myeloid cells or bone-marrow cells, peripheral mononuclear cells, myeloid mononuclear cells, somatic stem cells, and pluripotent cells in addition to the aforementioned cartilage cells, while examples of the foregoing tissues include ones selected from the group consisting of skin tissues (such as epidermal tissues and dermal tissues), bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues, in addition to the aforementioned cartilage tissues.

According to an embodiment of the method for the production of a porous body, which is herein provided by the present invention, the porous body consisting of a silk protein and having a thin film surface and a porous surface can be produced by introducing an aqueous solution of a silk protein derived from domesticated silkworms or wild silkworms such as silk fibroin or silk sericin, to which a water-soluble organic solvent is added in an amount ranging from 0.05 to 10% by volume, into a mold having a shape such as a box-like one and having a bottom or top surface which has been surface-roughened by sticking or adhering, for instance, filter paper, a nonwoven fabric, or a surface-roughened film onto the mold surface, or such a mold having a bottom or top surface which has been surface-roughened by mechanically or chemically treating the surface thereof; freezing the aqueous solution over a predetermined time period; and then thawing the frozen aqueous solution of the silk protein.

The aforementioned embodiments will hereunder be described in more detail.

In the present invention, materials used for the construction of the porous body having a thin film surface and a porous surface may be, for instance, biopolymers such as collagen and synthetic polymers such as polyesters, but they are preferably silk proteins consisting of silk fibroin and silk sericin while taking into consideration the ability thereof to form regenerated tissues and the mechanical properties thereof such as strength and elastic modulus. More preferably, the material is silk fibroin. The present invention will hereunder be described while mainly taking silk fibroin by way of example, but the following description concerning silk fibroin would hold true for silk sericin as well.

Silk fibroin used in the present invention may be any silk fibroin insofar as it is produced by silkworms such as domesticated silkworms and those inhabiting in the natural world including so-called wild silkworms and methods for the preparation thereof may likewise be any known one such as a method comprising the step of extracting the silk protein from the cocoons of such silkworms or a method comprising the step of extracting the protein from the silk glands of silkworms. In particular, the silk protein is preferably one extracted from the cocoons of domesticated silkworms because of the simplicity of the production process. In the present invention, silk fibroin is used in the form of an aqueous solution and such an aqueous solution of silk fibroin may be prepared according to any known technique and a specific example of such a method includes one in which silk fibroin dissolved in a lithium bromide aqueous solution is dialyzed against water.

In the present invention, it is intended to use this aqueous solution of silk fibroin as a raw material for the production of the porous body according to the present invention. In this connection, when such a porous body is used as a material employed in the fields of, for instance, the tissue-engineering and/or the regenerative medical engineering or a substrate or support for growing or cultivating cells, the aqueous solution may be subjected to the usual sterilization treatment using an autoclave at this stage. The concentration of the aqueous solution of silk fibroin used herein may arbitrarily be selected depending on the purpose of using the same, but it preferably ranges from 0.1% by mass to 10% by mass and more preferably 0.5% by mass to 5% by mass. This is because if the concentration thereof is less than 0.1% by mass, the resulting porous body does not always have satisfactory strength, while if it exceeds 10% by mass, the starting aqueous solution thereof can only be prepared with considerable difficulty and the use of the resulting porous body thus produced may sometimes adversely affect the proliferation and maintenance or conservation of the resulting tissues.

According to the present invention, a desired porous body can be produced by adding a water-soluble organic solvent to this aqueous solution of silk fibroin, maintaining the resulting mixture in its frozen state over a predetermined time period and then subjecting the frozen mixture to a thawing treatment.

The water-soluble organic solvent to be incorporated into the aqueous silk fibroin solution may be ones which may be miscible at least partially with water. Specific examples thereof include methanol, ethanol, propanol, isopropanol, butanol, isobutanol, sec-butanol, tert-butanol, isoamyl alcohol, glycerol, acetone, acetonitrile, dimethylformamide (DMF), dimethyl sulfoxide (DMSO), pyridine, acetic acid, butyric acid and lactic acid. Glycerol and dimethyl sulfoxide, which have widely been used as solvents for cell-storage, are preferably used since they have almost no adverse influence on biological tissues and cells. The amount thereof to be incorporated into the aqueous solution of silk fibroin is not limited to any specific range insofar as the use thereof is never accompanied by the formation of precipitates of silk fibroin when these organic solvents are added to the aqueous silk fibroin solution, but the amount thereof preferably ranges from 0.05% by volume to 10% by volume and more preferably 0.1% by volume to 5% by volume. This is because if the amount thereof is less than 0.05% by volume, any porous body is not formed in some cases, while if it exceeds 10% by volume, silk fibroin may be liable to cause precipitation and any porous body having sufficient mechanical strength cannot be produced.

The freezing temperature of the aqueous solution is not restricted to any particular one, but it may be one realized by the use of the usual freezer or the like, while taking the simplicity of the processing facility into account. The freezing of the aqueous solution may likewise be carried out while the solution is immersed in, for instance, cooled ethanol. The freezing time period may be one sufficient for completely freezing the aqueous solution of silk fibroin. It may vary depending on the size of the porous body to be produced, but it is preferably not less than 4 hours, and particularly preferably not less than 6 hours. If the freezing time period is less than 4 hours, any desired porous body cannot always be produced and the resulting porous body may sometimes have insufficient mechanical strength, although this may vary depending on the kind of freezer used.

The frozen aqueous solution of silk fibroin can be thawed just as it is to thus produce a porous body. The thaw of the solution can be carried out while warming the same, but it is usual that a porous body can more simply be produced by letting the frozen aqueous solution stand at room temperature.

In this respect, when using the resulting porous body as a material used in the fields of, for instance, the tissue-engineering and/or the regenerative medical engineering or as a substrate or support for cultivating cells, the porous body is subjected to the usual sterilization treatment in an autoclave after the water-soluble organic solvent previously added is replaced with water or a physiological buffer solution such as phosphate-buffered physiological saline (PBS) by the immersion of the porous body in the latter.

In the present invention, it is also possible to use modified silk fibroin obtained by the immobilization of a physiologically active molecule such as collagen, a cell factor and/or a cell adhesion factor on the silk fibroin molecule according to any known chemical modification technique. In addition, also usable herein include, for instance, modified silk fibroin products obtained using any known technique such as one, which makes use of gene-engineered recombinant silkworms, and the protein engineering technique.

According to the present invention, it is also possible that an aqueous solution of silk fibroin or a preliminarily sterilized aqueous solution of silk fibroin by the treatment thereof in an autoclave is blended with a physiologically active molecule such as collagen, a cell growth factor and/or a cell adhesion factor and that subsequently the resulting blend is treated by repeating the same procedures used above to thus form a porous body containing these molecules therein. Alternatively, it is likewise possible to blend, in the same manner used above, an aqueous solution of silk fibroin with chimera silk fibroin molecules obtained by fusing silk fibroin molecules with various kinds of physiologically active molecules and/or functional molecules according to the protein engineering technique and to then treat the resulting blend by repeating the same procedures used above to thus form a porous body containing these molecules therein. In this connection, when using the resulting porous body as a material used in the fields of, for instance, the tissue-engineering and/or the regenerative medical engineering or as a substrate or support for cultivating cells, it is rather preferred to use a preliminarily sterilized aqueous solution of silk fibroin by the treatment thereof in an autoclave, while taking into account the safety or the like. Moreover, it is also possible to use a porous body having a thin film surface and a porous surface after the impregnation of the porous body with a physiologically active molecule such as collagen, a cell growth factor and/or a cell adhesion factor.

Figure 1:
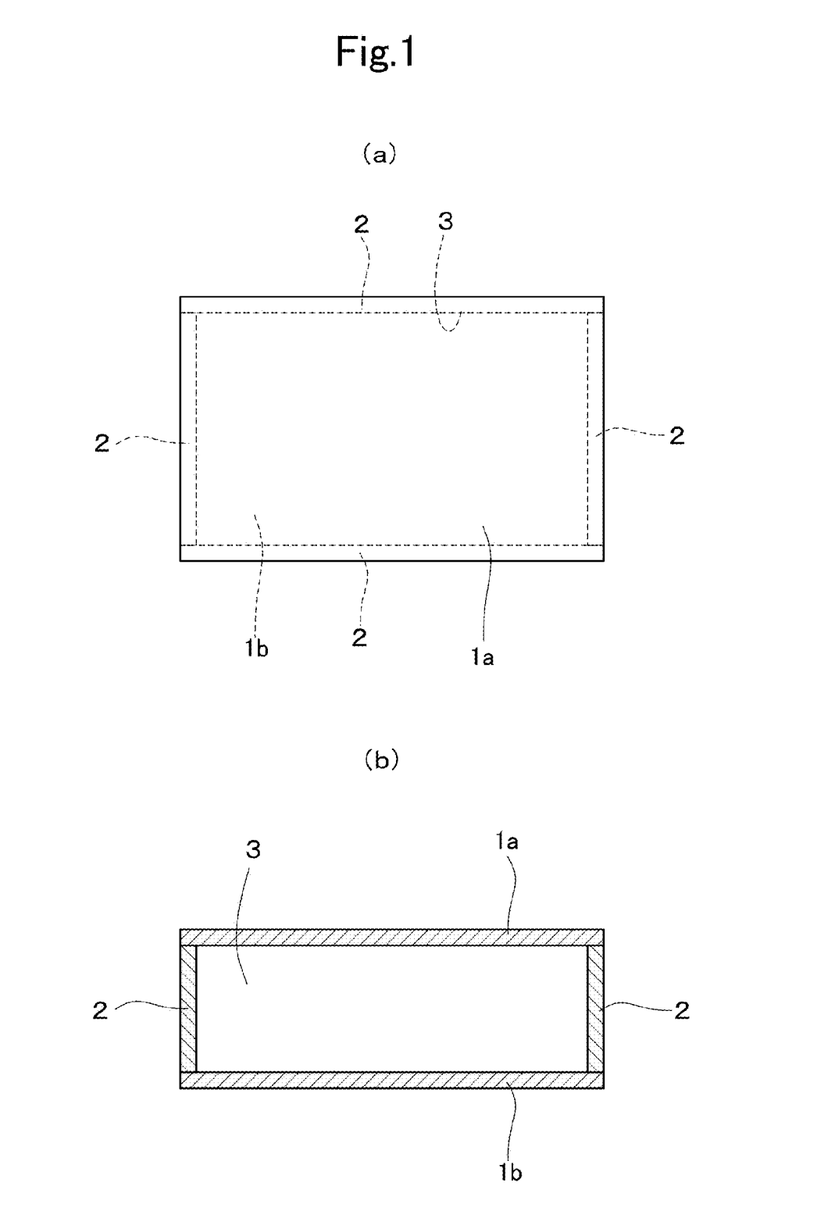
FIG. 1 is a schematic diagram showing an embodiment of a mold used for the production of a substrate for feeding cells and/or tissues according to the present invention, wherein FIG. 1(*a*) is a plan view of the mold and FIG. 1(*b*) is a cross sectional view thereof.

FIGS. 1(a) and 1(b) show an embodiment of the structure of the mold used for the production of a porous body according to the present invention, while making use of the foregoing material, in which FIG. 1(a) shows the top plan view of the mold and FIG. 1(b) shows a cross sectional view thereof. The porous body can be produced according to any known production technique and it is preferably produced according to a modification of the method disclosed in, for instance, Patent Document 3 specified above.

The mold as shown in FIG. 1 and usable in the present invention is composed of an upper acrylic plate 1a, a lower acrylic plate 1b and a spacer 2 and has a box-like shape within which a space 3 is formed. More specifically, the spacer 2 is arranged along the periphery or on the four sides of the acrylic plates 1a and 1b. The acrylic plate may be replaced with a plate made of, for instance, an organic material such as nylon, a vinyl chloride resin, an epoxy resin, or a phenolic resin; or a metallic material such as aluminum, brass, copper, or stainless steel. In addition, the spacer may be one made of, for instance, an elastomer such as silicone rubber, polyurethane, fluororubber or natural rubber; or one made of a metal such as aluminum and it is sufficient that the thickness of the spacer is one such that the resulting porous body can efficiently show the desired functions thereof. One surface of the acrylic plates 1a and 1b can be surface-roughened by sticking or pasting, for instance, filter paper, a nonwoven fabric, or a surface-roughened film on the corresponding surface, or by subjecting the corresponding surface thereof to a mechanical treatment (such as abrasion treatments), or to a chemical treatment (such as a treatment with an acid or a solvent, or a gas-etching treatment, or a treatment for coating the surface with a metal or an inorganic material according to a plasma-spray treatment).

The use of a box-like shaped mold having the structure discussed above would permit the production of a porous body having a thin film surface and a porous surface according to the present invention. More specifically, a raw material is introduced into this mold, the material included in the mold is allowed to stand in its frozen state over a predetermined time period and the frozen material is then thawed to thus produce a porous body consisting of silk proteins and having a thin film surface and a porous surface. In this case, the thin film surface is not formed on the side of the surface-roughened surface of the mold, but is formed on the side of the surface thereof free of any surface-roughening treatment. In this connection, the shape of the mold is not limited to any particular one insofar as it would permit the production of a desired porous body and accordingly, the mold may have a shape, other than a rectangular parallelepiped box-like one as shown in FIG. 1, such as a box-like shape having a circular cross section.

In the following Examples, a mold having a box-like shape as shown in FIG. 1 is used, which is constructed by the use of acrylic plates and spacers each composed of silicone rubber and having a thickness of 3 mm. A desired material is introduced into the space formed within the mold, the mold is then cooled to thus put the material included in the mold in deep-freeze over a predetermined time period, the frozen sample is thawed by letting the same to stand at room temperature and then the thawed sample is withdrawn from the mold to thus give an intended porous body.

When using the porous body thus produced as a substrate or support for cultivating cells (a substrate for feeding cells/tissues), for instance, an aqueous solution of silk fibroin is blended with a cell suspension, followed by the addition of a water-soluble solvent which never adversely affects the cells such as glycerol or dimethyl sulfoxide (DMSO) to the resulting blend and the subsequent repetition of the same procedures discussed above to thus produce a cell feeder which can undergo three-dimensional growth. Moreover, a cell feeder capable of undergoing three-dimensional growth can more simply be produced by adding a cell suspension to a porous body preliminarily produced to thus make the cells gradually penetrate into the interior of the porous body. When comparing collagen widely and conventionally used as a three-dimensional cell-growth support with the porous body used in the present invention, it is found that the porous body of the present invention shows the following features: it is easy for the porous body of the present invention to control the void volume and the pore size thereof; the porous body of the present invention does not undergo any conspicuous shrinkage or the reduction of the volume thereof; and the porous body permits the more efficient growth of cells.

The thin film on the surface of the foregoing porous body may be one having any shape and mechanical properties inasmuch as it shows an effect of protecting damaged sites or the like and a sufficient tear strength upon the fixation thereof through suture, but it should preferably have flexibility almost identical to that of the porous body to ensure the achievement of the desired protective effect. The thickness of the thin film is not restricted to any particular one inasmuch as it can satisfy the foregoing requirements, but the thickness thereof preferably falls within the range of from 1 to 2,000 µm and more preferably 10 to 100 µm. It is sufficient for the thin film to have a tear strength which would ensure the fixation of the porous body to an affected part through suture, but the tear resistance thereof is preferably not less than 0.05N and particularly preferably not less than 0.1N as expressed in terms of the values as determined according to the Trouser Tear Method (JIS K7128).

The pore size of the porous body is not restricted to any particular level insofar as the use of the porous body would permit the excellent progress of the tissue-regeneration and it ranges from about 50 to 500 µm and preferably 80 to 300 µm. This is because the use of a porous body whose pore size is less than 50 µm makes it unfavorable to form tissues extending from the surface to the interior of the porous body, while if it exceeds 500 µm, the resulting porous body is insufficient in its mechanical strength and the use of such a porous body makes it difficult to regenerate tissues in the proximity to the surface of the porous body. The thickness of the porous body is not limited to any particular level insofar as the porous body is in conformity with the size of the tissue to which it is applied and the body has appropriate cushioning characteristics, but it ranges from 1 mm to 100 mm and preferably 1 mm to 20 mm. This is because if the thickness thereof is less than 1 mm, the cushioning characteristics of the resulting porous body is unsatisfied, while if it exceeds 100 mm, the resulting porous body can only be fixed to a tissue-defective site with great difficulty. In addition, in respect of the mechanical characteristics of the porous body, the tensile strength of the body is preferably not less than 0.01 MPa, while taking into consideration the handling properties and the ability of the body to protect damaged tissues from the adverse effect of mechanical load possibly applied thereto.

In addition to those described above, methods for the production of a porous body consisting of silk fibroin and having a thin film surface and a porous surface, which can be adopted herein, include, for instance, a method in which a thin film and a porous body are separately prepared and then adhered them to each other; a method in which a porous body carrying thin films on the both sides thereof is produced in advance and one side thereof is then cut off; and a method comprising the steps of forming a porous body and then forming a thin film on the surface of the porous body. However, these methods comprise complicated steps and therefore, the practice thereof would be unfavorable from the industrial standpoint. For this reason, it would be preferred, like the present invention, that an aqueous silk fibroin-organic solvent mixed solution is introduced into a box-like mold, as illustrated in FIG. 1, in which filter paper or a nonwoven fabric has been stuck to the bottom surface thereof, or whose bottom surface has been surface-roughened in advance by a mechanical treatment or a chemical treatment, and then the mixed solution contained in the mold is subjected to freezing and thawing treatments; or that an aqueous silk fibroin-organic solvent mixed solution is introduced into a mold whose one side has been surface-roughened in the same manner described above, the mixed solution contained in the mold is immersed in a coolant such as cold ethanol and then subjected to freezing and thawing treatments. Thus, a porous body having a thin film surface and a porous surface can easily be produced. In this case, a thin film is formed on the surface of the porous body on the side free of any stuck filter paper or nonwoven fabric or free of any surface-roughening treatment, while any thin film is not formed on the side of the porous body, which carries filter paper or a nonwoven fabric stuck thereto or which is surface-roughened and the latter thus serves as a porous surface.

Seed cells capable of regenerating a target damaged tissue are inoculated or seeded on a porous body, as has been discussed above, which has a thin film surface and a porous surface, or regenerated tissues are formed by cultivating such seed cells under the known conditions (for instance, the cells are cultivated in the usual cell culture medium or a culture medium containing a growth factor or a differentiation- or specialization-inducible factor in an environment maintained at 37° C. and 5% $CO_2$; or under the application of a load by the action of a centrifugal force or a hydraulic pressure, or under the application of a shearing stress generated by rotating the porous body), the porous surface of the porous body is brought into close contact with the surface of a damaged tissue and then fixed thereto by suturing through the thin film surface. Thus the regeneration of the damaged site would be stimulated and/or accelerated. The cells and tissues used herein are not restricted to particular ones insofar as they can regenerate target damaged and/or defective tissues, but usable herein as such cells and tissues include somatic stem cells such as myeloid cells or bone-marrow cells, peripheral mononuclear cells, myeloid mononuclear cells and myeloid stem cells; pluripotent cells such as ES cells and iPS cells, in addition to the cells derived from every corresponding tissues. Thus tissues are excellently regenerated due to such effective actions as the firm and stable fixation by the suture through the thin film surface, the protection of the damaged sites or the like, the migration of cells or tissues from the tissues formed on the porous surface, and the protection of the damaged sites from any mechanical load due to the cushioning characteristics of the porous body. In addition, the achievement of an additional effect may also be anticipated, which would be accomplished due to the migration of humoral molecules such as cytokine which serves to accelerate and control the tissue regeneration and which is produced by the cells and/or tissues present in the porous material to the surface of damaged tissues or tissue-defective sites. For instance, cartilage tissues can be formed on the porous surface using cartilage cells, followed by bringing the surface of the resulting cartilage tissue into close contact with the surface of a joint cartilage-defective site and the subsequent suture of the porous body and the joint cartilage-defective site through the thin film surface of the body to thus sufficiently and stably fix the porous material to the joint surface. Thus the defective joint surface is protected from any mechanical load possibly applied thereto, while cartilage cells migrate from the surface of the tissues formed on the body to the defective site and as a result, cartilage tissues are excellently regenerated.

The cell/tissue feeder according to the present invention, which is fixed, through suture, to the surface of defective and/or damaged tissues may be maintained on the affected site as it is unless any inconvenience occurs and the cell/tissue feeder transplanted may likewise be removed from the affected site after confirming if the desired tissues are sufficiently regenerated.

As has been discussed above in detail, the present invention thus permits the production of a porous body consisting of silk proteins and having a thin film surface and a porous surface, with ease. In this respect, the thin film surface never serve as an obstacle in the regeneration of tissues, but the thin film surface can provide sufficient strength for the realization of excellent fixation, through suture, to the surface of a wound and can simultaneously be effective for the protection of the surface thereof. Moreover, the porous surface of the porous body may serves as a good place or area for the tissue-regeneration and also serves as a cushioning material capable of relieving any mechanical load possibly applied onto the surface of a wound. The cell/tissue feeder according to the present invention simultaneously permits the differentiation and proliferation of cells in vitro, can stimulate and accelerate good regeneration of tissues using only a small number of initial cells and can promote the excellent tissue regeneration in vivo while acting as a transplant of cells or tissues. Furthermore, the cell/tissue feeder according to the present invention can likewise be applied to the surface of a large wound which is completely defective in cells and tissues.

The tissue-regeneration treatment according to the present invention, which makes use of the porous body consisting of silk proteins and having a thin film surface and a porous surface likewise according to the present invention, can widely be applied to a variety of fields, for instance, the cartilage regeneration (in the cases of diseases such as osteoarthritis (arthritis deformans), chronic rheumatism, and traumatic cartilage deficiency), the regeneration of the skin (in the case of, for instance, burn), the regeneration of subcutaneous tissues (in the case of, for instance, cartilage tissue deficiency over a wide area due to trauma, surgical operations or the like, necrosis, and incurable wounds), the prevention of adhesion (abdomen, tendon of hand and finger or the like), the repair of cornea, the repair of tympanic membrane, the reinforcement of aneurysm, the repair of nerve, the repair of periodontal membrane, hernia patches, the treatment of bedsore, bladder patches, the patches for damaged myocardial sites, the treatment of damaged intra-abdominal organs (in the cases of, for instance, ulcer of digestive tract (enteric ulcer), perforation of digestive tract (enteric perforation), hepatorrhexis, and the reinforcement of the anastomosed region of digestive tract and the excised regions of organs), the treatment of pneumothorax, and the reinforcement of colostomy (in the case of an artificial anus). Moreover, these tissue regeneration techniques can be applied not only to the medical treatment of human beings, but also to the treatment of wounds and/or diseases of pet animals such as canines and felines as well as to the treatment of wounds and/or diseases of domestic animals such as cattle and equines.

Example 1

Illustrated in this Example 1 is an embodiment of a method for the production of a substrate consisting of silk fibroin, which is a porous body consisting of silk fibroin and having a thin film surface and a porous surface.

Refined silk fibers derived from domesticated silkworms were dissolved in a 9M aqueous solution of LiBr and then the resulting solution was sufficiently dialyzed against distilled water to thus prepare an 8 wt % aqueous silk fibroin solution. To the 8 wt % aqueous silk fibroin solution, there was gradually dropwise added an equal volume of a DMSO aqueous solution whose concentration had been adjusted in such a manner that the final concentration of DMSO was equal to 1% by volume, while sufficiently mixing the resulting mixture so as not to entrain partial coagulation of fibroin. The resulting silk fibroin-DMSO mixed aqueous solution was introduced into the internal space of a box-like mold (as shown in FIG. 1), which had been assembled using upper and lower acrylic plates, and silicone rubber plates each having a thickness of 3 mm, positioned between the upper and lower acrylic plates and serving as spacers, and then the mixed aqueous solution was subjected to a freezing treatment by immersing the mold containing the solution in cold ethanol (cooled to −20° C.) for a period of time of not less than 6 hours. The frozen sample was thawed at room temperature and then removed from the mold to thus give an intended porous body.

Figure 2:
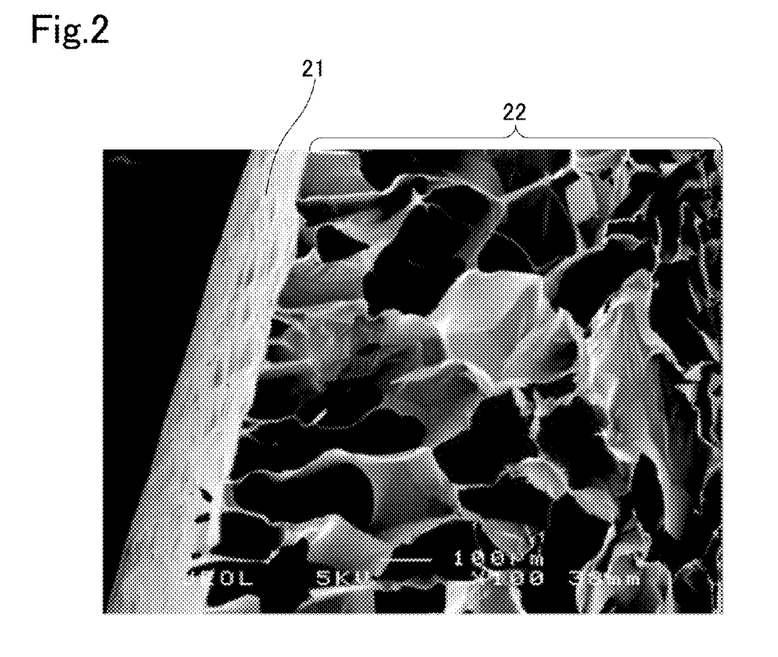
FIG. 2 is an SEM micrograph showing the cross section of the substrate composed of silk fibroin and produced in Example 1.

In the foregoing production of the porous body, the inner surface of an acrylic plate serving as one side of the mold was surface-roughened, in advance, by sticking filter paper to the surface. As a result, a thin film was formed on the surface of the resulting porous body on the side which came in close contact with the inner surface of the mold free of filter paper, while any thin film was not formed on the surface of the resulting porous body on the side which came in close contact with the inner surface of the mold to which the filter paper had been stuck. There was thus produced a porous body consisting of silk fibroin and having a thin film surface and a porous surface. The porous body thus produced was immersed in water over a period of time sufficient for the removal of the DMSO included therein. FIG. 2 is an SEM micrograph showing a cross sectional view of the silk fibroin substrate or the porous body thus produced. In FIG. 2, the reference numerals 21 and 22 represent the thin film surface and the porous surface of the resulting porous body, respectively.

Example 2

Illustrated in this Example 2 is an embodiment in which cartilage tissues are formed on the substrate consisting of silk fibroin, which was the porous body produced in Example 1.

Figure 3:
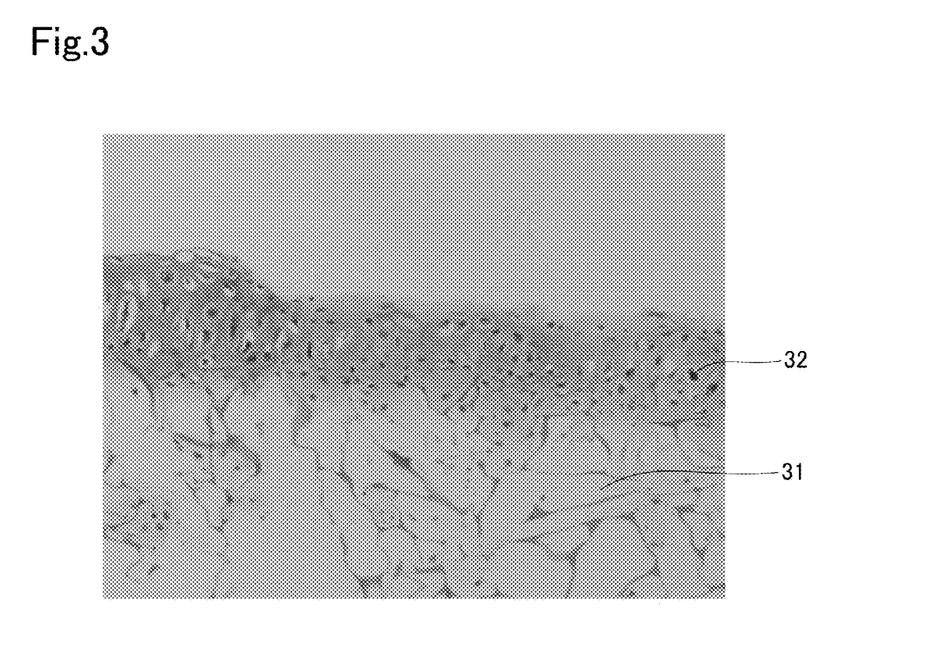
FIG. 3 is an SEM micrograph showing the cartilage tissues (stained with Saffron-O) formed on the porous surface of the substrate composed of silk fibroin and produced in Example 2.

The substrate consisting of silk fibroin produced in Example 1 was cut into disk-like pieces each having a diameter of 8 mm (the thickness thereof was 3 mm), cartilage cells prepared from the articular cartilage originated from a Japanese white domesticated rabbit were inoculated on the porous surface of the disk-like piece at a density of $1.5 \times 10^6$ cells/disk (diameter 8 mm; thickness 3 mm) and then the cells were cultivated in a cell culture medium (DMEM containing 10% FBS) at 37° C. and 5% $CO_2$ for 2 weeks, using an incubator, under the static conditions to thus form cartilage tissues. Most of the inoculated cartilage cells were present on the outer layer of the porous surface of the body and the cartilage tissues were formed on the surface of the porous surface starting from the cartilage cells. In this connection, FIG. 3 is an SEM micrograph illustrating the cartilage tissues (stained with Saffron-O) thus formed on the porous surface of the silk fibroin substrate produced above. In FIG. 3, the reference numerals 31 and 32 represent the porous surface of the body and the cartilage tissues formed on the porous surface and stained with Saffron-O, respectively.

As has been described above, it was found that cartilage tissues can be formed by the cultivation or seeding of cartilage cells inoculated on the silk fibroin substrate prepared in Example 1 and accordingly, this clearly indicates that if a desired quantity of cells, other than cartilage cells, selected from the group consisting of myeloid cells, peripheral mononuclear cells, myeloid mononuclear cells, somatic stem cells, and pluripotent cells are inoculated on the porous surface of the silk fibroin substrate, each corresponding tissue can likewise be produced.

Example 3

In this Example 3, an experiment was carried out, in which the cartilage tissues produced in Example 2 were embedded or implanted into a Japanese white domesticated rabbit.

Figure 4:
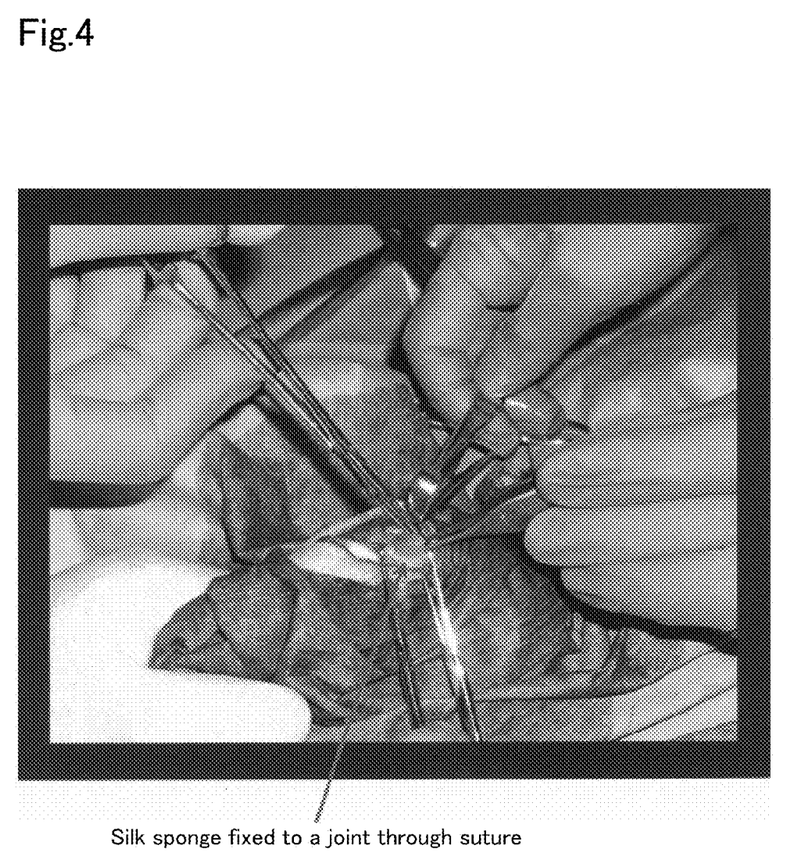
FIG. 4 is a photograph showing the cartilage tissue formed on a substrate made of silk fibroin (silk sponge) obtained in Example 3, in which the cartilage tissue is fixed and adhered to a tissue defective surface of a patellar joint by suturing the substrate and the site in such a manner that the patellar joint is completely covered with the substrate and that the thin film surface of the substrate faces the tissue-deficient surface.

After applying general anesthesia to a Japanese white domesticated rabbit, the knee joint was opened and exposed according to the internal para-patellar approach (patellectomy) to expose the surface of the patellar joint and then the cartilage tissues present on the surface of the both patellar joints were completely scraped off. Then, for one of these knees, the silk fibroin substrate produced in Example 2, on which cartilage tissues had been formed, was applied onto the exposed patellar joint surface and fixed thereto by suture through the thin film surface, in such a manner that the cartilage tissue-carrying side of the substrate faced the joint surface and that the joint surface was completely covered with the substrate. On the other hand, for the other knee as a control, the same silk fibroin substrate free of any cartilage tissue cultivated thereon was fixed to the joint surface by suturing the same through the thin film surface as in the same manner used above. FIG. 4 shows the silk fibroin substrate which is fixed to the joint surface through suturing them. Then the patella was repositioned, the skin was sutured and the test animal was then kept. After the elapse of 6 weeks, the test animal was euthanatized, the tissues were isolated and a photographic image of the tissues was taken and observed.

It was found that the test animal could give hopping motions even after one day from the operation. According to the histological sign, it was observed that the formation of glassy or vitreous cartilage tissues was observed on the patellar joint surface of the animal group in which the silk fibroin substrate carrying cartilage tissues previously formed thereon was used. On the other hand, there was not observed the formation of any cartilage tissue for the animal group as a control, in which only the silk fibroin substrate free of any cartilage tissue was used.

Figure 5:
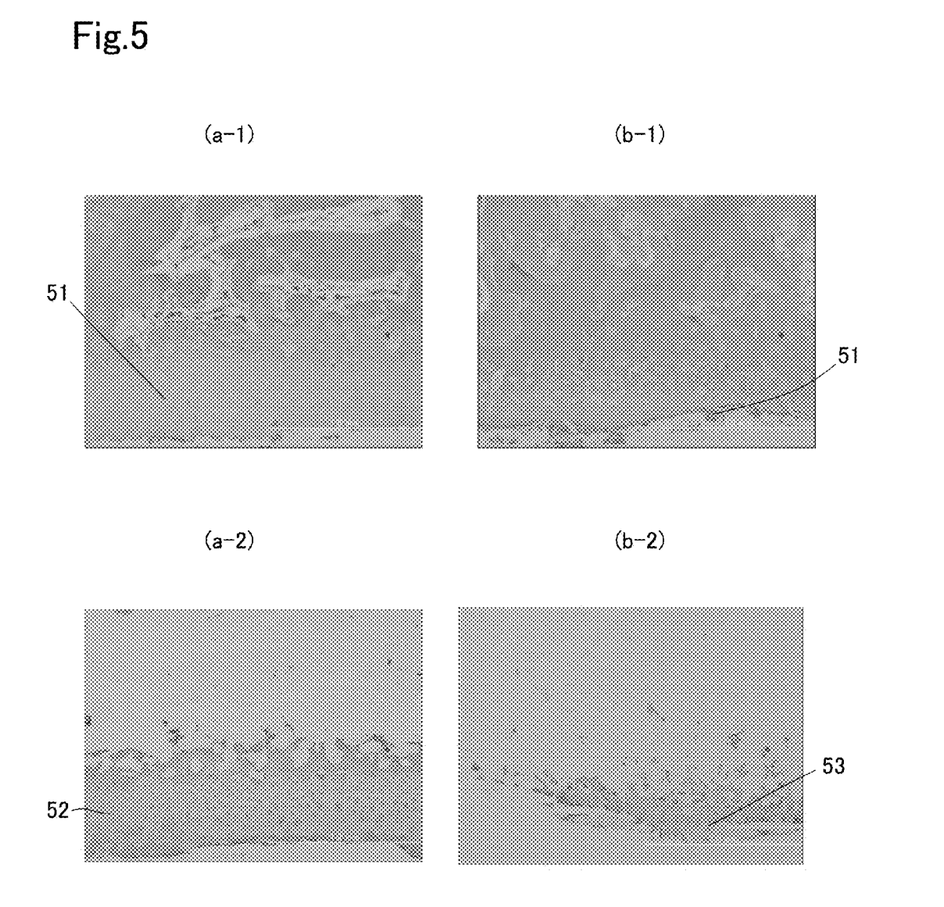
FIG. 5 shows photographs each illustrating the image of tissues formed on the surface of a patellar joint, which is produced in Example 3 and more specifically, FIG. 5(*a*-1) is an image of tissues obtained using a substrate made of silk fibroin on which cartilage tissues have been formed in advance, wherein the surface of the patellar joint is stained with H.E. (hematoxylin-eosin staining)

Photographic images of the tissues formed on the patellar joint surface observed for the Japanese white domesticated rabbits which had been subjected to the foregoing treatments are shown in FIGS. 5(*a*-1), 5(*a*-2), 5(*b*-1) and 5(*b*-2). More specifically, FIGS. 5(*a*-1) and 5(*a*-2) show the histological images observed when the silk fibroin substrate carrying cartilage tissues previously formed thereon was used, while FIGS. 5(*b*-1) and 5(*b*-2) show the histological images observed when only the silk fibroin substrate free of any cartilage tissue was used. Further FIGS. 5(*a*-1) and 5(*b*-1) show the histological images observed when the patellar joint surface was subjected to the H.E. staining, while FIGS. 5(*a*-2) and 5(*b*-2) show the histological images observed when the cartilage tissues were subjected to the Collagen II immunostaining. In FIG. 5, the reference numeral 51 represents the patellar joint surface subjected to the H.E. staining, while the reference numerals 52 and 53 represent the cartilage tissues subjected to the Collagen II immunostaining. As will be clear when comparing FIG. 5(*a*-2) with FIG. 5(*b*-2), quite excellent cartilage tissues are regenerated in the case wherein the silk fibroin substrate carrying cartilage tissues previously formed thereon is used.

Figure 6:
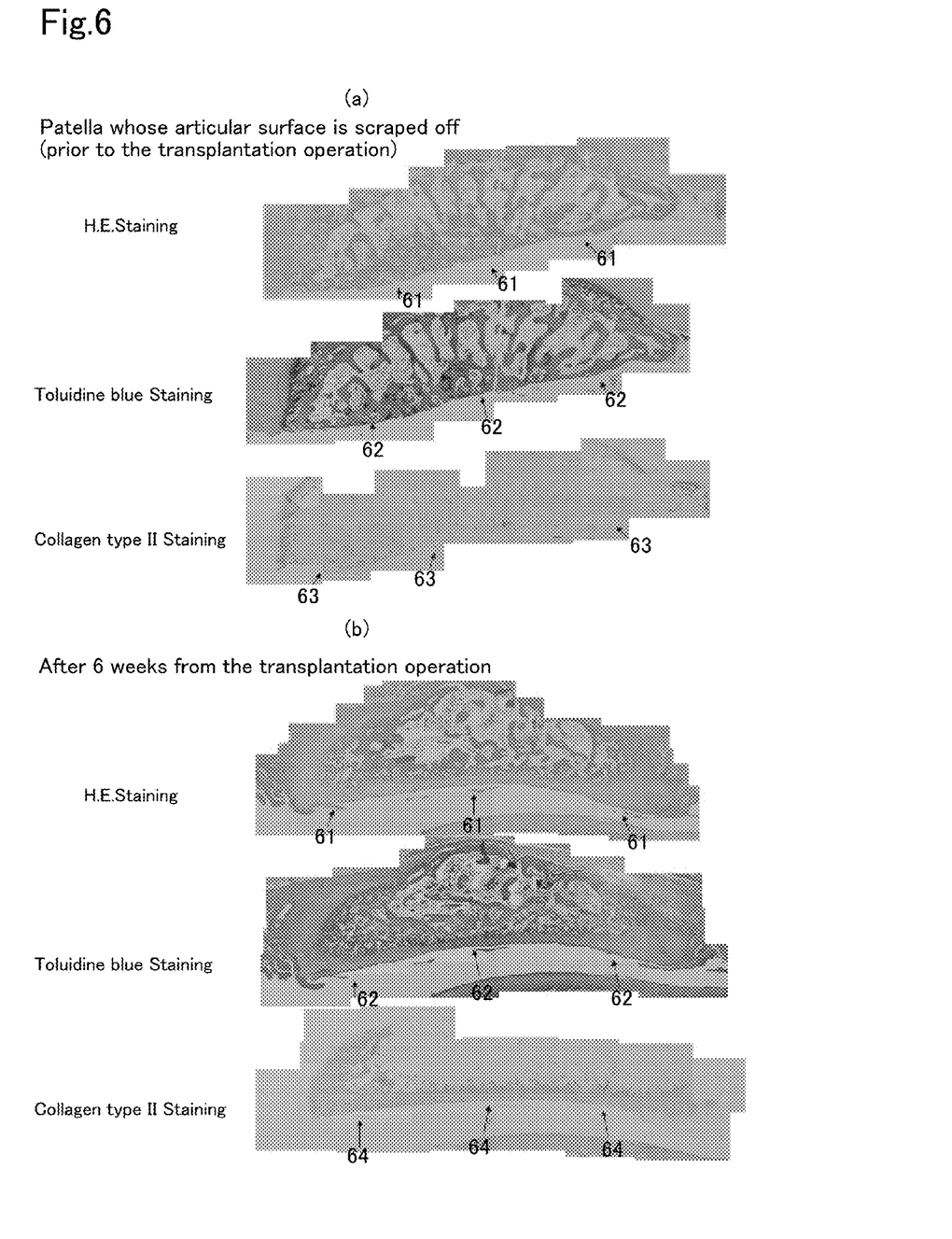
FIG. 6 shows photographs each illustrating the condition of articular cartilage regenerated using a substrate made of silk fibroin in Example 3. More specifically, FIG. 6(*a*) shows an image of the tissues of a patellar joint from which the cartilage tissues have completely been removed prior to the transplantation of a substrate composed of silk fibroin.

In addition, there was observed the formation of good cartilage tissues over the whole joint surface for the test animal group in which the silk fibroin substrate carrying cartilage tissues previously formed thereon was used, even when observing the entire joint surface of the foregoing specimens (see FIG. 6).

FIG. 6 shows photographs or histological images each illustrating the condition of articular cartilage regenerated using the foregoing substrate made of silk fibroin. More specifically, FIG. 6(*a*) is a histological image of the patella from which the cartilage tissues present on the whole joint surface are completely removed prior to the transplantation of a substrate composed of silk fibroin; and FIG. 6(*b*) shows a histological image of the patella observed after 6 weeks from the transplantation of the substrate. The results as shown in these figures clearly indicate that cartilage tissues are regenerated over the whole joint surface. In FIGS. 6(*a*) and 6(*b*), the reference numerals 61 and 62 represent the cartilage portions prior to and after the transplantation of the substrate and which are subjected to the H.E. staining and the Toluidine blue staining, respectively and the reference numerals 63 and 64 represent the cartilage surfaces (cartilage tissues) prior to and after the transplantation of the substrate and which are subjected to the Collagen II immunostaining, respectively. As indicated by the reference numeral 63 in FIG. 6(*a*), it would be recognized that the cartilage tissues are completely removed from the patellar joint surface and as indicated by the reference numeral 64 in FIG. 6(*b*), it would likewise be recognized that cartilage tissues are regenerated over the whole joint surface.

Thus, the use of the tissue-feeder provided thereon with cartilage tissues according to the present invention would permit the treatment of a damaged cartilage tissue even when it is quite widely damaged and extends over the whole surface of the cartilage tissue. The treatment of such a widely damaged site is a case which has been considered to be quite difficult to ensure the healing thereof, but the foregoing indicates that the present invention would permit the achievement of a considerably conspicuous healing effect for such a treatment.

In the meantime, after the desired cartilage tissues are formed, the silk fibroin substrate can, if necessary, be removed from the initially damaged site.

Example 4

Using Japanese white domesticated rabbits, the same procedures used in Example 3 were repeated except for the following points to evaluate the present invention with respect to the tissues taken from the domesticated rabbits. More specifically, as in the case of Example 3, there was observed the state of the cartilage tissues on the patellar joint surface, which was regenerated (or repaired) through the use of the silk fibroin substrate carrying the cartilage tissues preliminarily formed thereon and produced in Example 2 and there was also observed the conditions of the articular cartilage on the surface opposed to that of injured site (the surface of the lateral joint of femur) during the term of the cartilage tissue-regeneration. Incidentally, as a control, also observed herein according to the same procedures was the condition of the patellar joint surface from which the cartilage tissues had completely been cut off (the cartilage deficiency-formed (severe OA) state), wherein any silk fibroin substrate was not used, unlike the case of Example 3.

According to the histological observation, observed herein for the test animal group, in which the silk fibroin substrate carrying the cartilage tissues previously formed thereon was used, was the formation of excellent vitreous cartilage tissues on the patellar joint surface. On the other hand, the formation of any cartilage tissue was not observed at all for the test animal group, as a control, wherein any silk fibroin substrate was not used.

Figure 7:
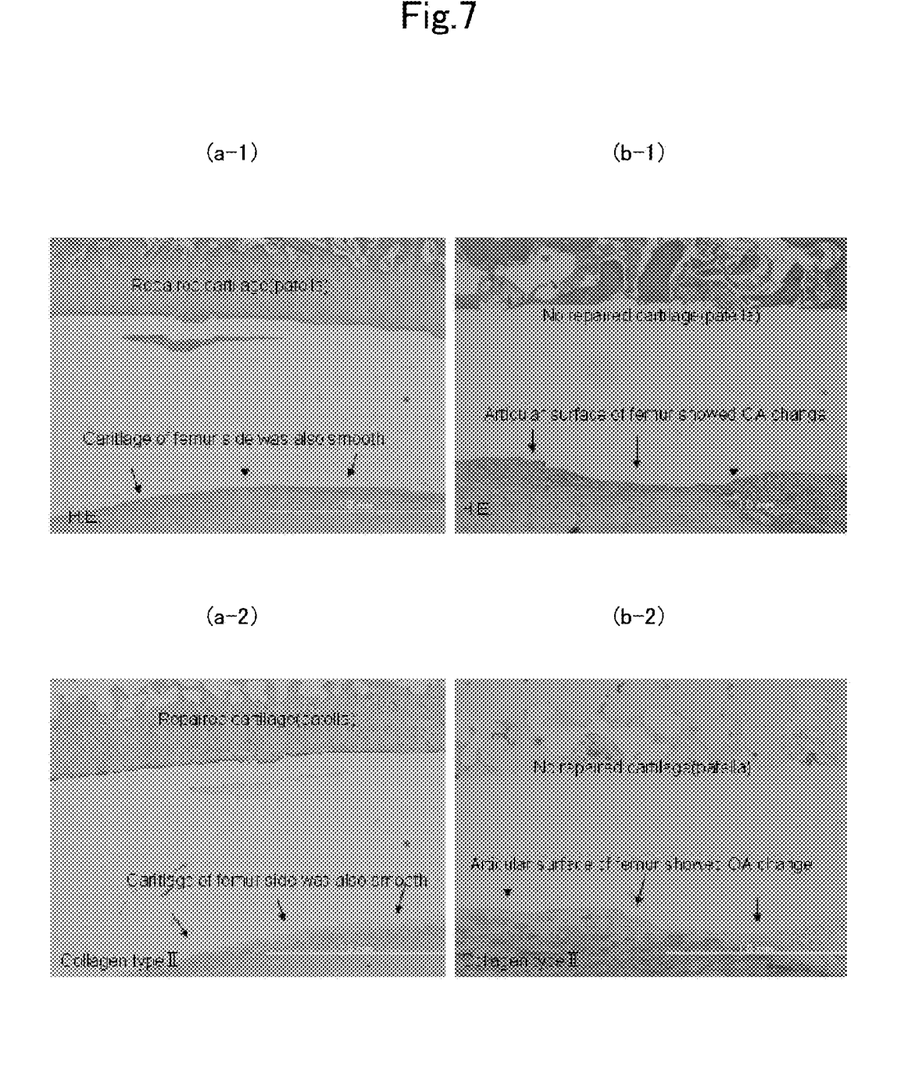
FIG. 7 shows photographs each illustrating tissular images of tissues formed on the surface of the patellar joint and the surface opposed thereto and more specifically, FIGS. 7(*a*-1) and (*a*-2) show tissular images of tissues observed when using a substrate composed of silk fibroin on which cartilage tissues have been formed in advance and FIGS. 7(*b*-1) and (*b*-2) show tissular images of tissues observed when any substrate composed of silk fibroin is not used and, in other words, these figures each show the tissue in its cartilage defective state.

Photographs illustrating tissular images of tissues formed on the surface of the patellar joint and the surface opposed thereto are shown in FIGS. 7(*a*-1), 7(*a*-2), 7(*b*-1) and 7(*b*-2). More specifically, FIGS. 7(*a*-1) and 7(*a*-2) show histological images of tissues observed when using a substrate composed of silk fibroin on which cartilage tissues have been formed, in advance, and FIGS. 7(*b*-1) and 7(*b*-2) show histological images observed when any substrate composed of silk fibroin is not used (control). Further specifically, FIGS. 7(*a*-1) and 7(*b*-1) show histological images observed for the patellar joint surface and the surface opposite to the same, which are subjected to the H.E. staining, and FIGS. 7(*a*-2) and 7(*b*-2) show histological images illustrating the cartilage tissues which are subjected to the Collagen II immunostaining.

As will be clear from FIGS. 7(*a*-1) and 7(*a*-2), it would be recognized, if using a silk fibroin substrate carrying the cartilage tissues previously formed thereon, that quite excellent cartilage tissues are regenerated during the term of the cartilage-regeneration process on the surface of the patellar joint; that the silk fibroin substrate ensures the effect of protecting not only the patellar joint surface, but also the articular cartilage present on the surface on the side opposed to the former (the surface of the lateral joint of femur) and that these surfaces are thus maintained in their smooth or even conditions. Contrary to this, the data as shown in FIGS. 7(*b*-1) and 7(*b*-2) clearly indicate that if allowing the cartilage deficiency-formed state to stand as it is, without using any silk fibroin substrate, not only any cartilage tissue cannot be regenerated, but also the surface opposed to that of the cartilage-deficient site is damaged and as a result, the joint surface of femur suffers from arthritis deformans. In FIGS. 7(*a*-1), 7(*a*-2), 7(*b*-1) and 7(*b*-2), the term "Repaired cartilage (patella)" means "regenerated cartilage (on the surface of patella)"; the passage "Cartilage of femur side was also smooth" means "the cartilage on the femur surface was smooth"; the term "No repaired cartilage (patella)" means "non-regenerated cartilage surface (patellar joint surface)", and the passage "Articular surface of femur showed OA change" means "articular joint surface of femur was in its condition afflicted with arthritis deformans".

Accordingly, it can be recognized that the use of the cell/tissue feeder carrying cartilage tissues preliminarily formed thereon, according to the present invention, would ensure the achievement of not only the effect of protecting cartilage during the process for the cartilage-regeneration on the patellar joint surface, but also the surface opposite to the cartilage and that these surfaces are thus maintained in their smooth or even conditions. As has been described above in detail, the use of the cell/tissue feeder permits the protection of the surface opposite to the damaged or defective cartilage tissues as well and therefore, this clearly indicates that the present invention can ensure the achievement of a quite conspicuous healing effect.

As has been discussed above in detail, it was proved, in Examples 3 and 4, that cartilage tissues are regenerated on the whole joint surface in the experiments carried out using the cartilage tissues formed in Example 2. This indicates that the cell/tissue feeder according to the present invention can likewise be applied to the regeneration of tissues selected from the group consisting of skin tissues, bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues, in addition to the aforementioned cartilage tissues.

As the methods for medically treating human being and/or animals while using the aforementioned substrate for feeding cells and/or tissues according to the present invention or the techniques of the regenerative medical treatments, they comprise the following processes if using, for instance, cartilage cells/tissues:

(1) A step of inoculating seed cells on the substrate for feeding cells/tissues;
(2) Arthroplasty (for instance, the preparation of articular environment by, for instance, the formation of bone);
(3) Operations for promoting or accelerating the cartilage-regeneration (for instance, the formation of a subchondral bone or the like);
(4) The fixation of a cell/tissue feeder to an affected site; and
(5) The guidance of a patient in conducting the movement of his joint after the operation thereof.

In the cases where a sufficient number of cells are present in the marrow in the proximity to an affected site, the foregoing step (1) can be omitted, and the aforementioned step (4) may be the fixation of the substrate for feeding cells and/or tissues to the affected site. Moreover, the arthroplasty as specified in the item (2) is a plastic operation of the environs of a joint such as the high tibial osteotomy, and the operation for promoting or accelerating the cartilage-regeneration as set forth in the item (3) is the operation for forming a subchondral bone such as the abrasion operation. In other words, these two steps (2) and (3) may appropriately or arbitrarily be selected depending on the conditions of affected sites. Furthermore, various kinds of methods would be conceivable, as the methods of guiding patients in the way how to move their joints after the operation thereof. Accordingly, the principal medical treatments proposed above are (1) the inoculation of seed cells on the substrate for feeding cells and/or tissues to (4) the fixation of a cell/tissue feeder to an affected site listed above. In this respect, the term "abrasion operation" means an operation in which an intended cartilage tissue is shaved off (cut off) to some extent.

The bone not only is flexible, but also has high-grade mechanical functions such that it may undergo sliding motions, while withstanding a high stress on the order of not less than 10 MPa. The following would be the key to the cartilage-regeneration medical treatment: The way how to support such loads possibly applied to an afflicted joint and to allow the joint to perform desired motions could be established, till the intended cartilage tissues acquire the desired mechanical functions. According to the medical treating method proposed above, the presence of the thin film surface of the porous body can serve to prevent the occurrence of any dissipation of the cells to be converted into cartilage tissues from an affected site, also serves to isolate the affected site from other cells present in the articular cavity and further serves to prevent any breakage of the porous body due to any possible contact and/or sliding motions between the affected site and the surface opposite to the joint. For this reason, a substrate for feeding cells and/or tissues (or a cell/tissue feeder) should be closely adhered to and firmly fixed to the affected site to be treated. This would be ensured by the use of the substrate for feeding cells/tissues (or the cell/tissue feeder) according to the present invention.

The operation methods can be divided into the following two groups: The known operation using a retractor in which the skin or the like are incised to thus open the region in the vicinity to the affected site and the porous body is then fixed thereto under the observation with the naked eyes; and the known operation in which the porous body is fixed under the observation with an endoscope. In the fixing method according to the operation using a retractor, the porous body can be fixed by tacking the same on the cartilage tissues in the vicinity of the affected site with a suture or the body can likewise be fixed to a desired position through the use of a device for fixation, while in the case of the fixation according to the operation carried out under the observation with an endoscope, it would be necessary to use a specially designed device for fixation. If using, for instance, "a tool for fixing a prosthetic material to a defective tissue" as disclosed in FIGS. 2A to D of Japanese Un-Examined Patent Publication No. 2006-230874, as such a device for fixation, the body can be fixed to an affected site without opening the site to such an extent. In the FIG. 2A, a cell/tissue feeder, as a tissue-prosthetic material represented by the reference numeral 6, is firmly fixed to a defective cartilage (affected site) represented by the reference numeral 7 by the insertion of the anchor member of the feeder represented by the reference numeral 2 into the corresponding bone.

The site, to which the cell/tissue feeder is to be fixed, is selected from the group consisting of, for instance, knee joint, medial malleolus, lateral malleolus, patellar joint of femur (patellofemoral joint), hip joint, and all of other joints as well as the surface of defective tissues.

The foregoing therapeutic method comprises, for instance, the steps of inoculating or seeding a variety of cells capable of being used in the present invention such as those listed above onto the surface of the substrate for feeding cells/tissues, which consists of a porous body having a thin film surface and a porous surface according to the present invention; cultivating the inoculated or seeded cells to form a cell/tissue feeder carrying the corresponding tissues formed thereon; and then fixing the resulting cell/tissue feeder, by suturing the same through the thin film surface of the feeder, to the affected site of a patient, for instance, tissues, organs, parts or systems, which are insufficient or defective in their shapes or functions, such as knee joint, medial malleolus, lateral malleolus, patellar joint of femur (patellofemoral joint), hip joint, and all of other joints, or the surface of tissues such as those defective in their tissues to thus treat the foregoing affected sites.

In the aforementioned therapeutic methods, if a sufficient number of cells are present in the marrow in the proximity to an affected site, it is also possible to treat a damaged site of a patient such as a tissue, an organ or a part or system, which are insufficient or defective in their shapes or functions, by applying the substrate for feeding cells/tissues consisting of the porous body, which has a thin film surface and a porous surface, according to the present invention, to the damaged site, while adhering and fixing the porous body to the damaged site by the suture of the damaged site and the porous body through the thin film surface of the porous body.

If using, for instance, cartilage cells and/or tissues prior to the fixation of the substrate for feeding cells and/or tissues or the cell/tissue feeder to the damaged site, the aforementioned therapeutic method comprises the steps of carrying out the arthroplasty such as the maintenance of the mechanical environment of a joint (for instance, the peri-arthroplasty such as the high tibial osteotomy), which is appropriately selected depending on, for instance, the conditions of the affected site and then conducting the operation for promoting the cartilage regeneration, for instance, the formation of subchondral bone or tissues (for instance, the operation for forming subchondral bone such as the abrasion operation), which is likewise appropriately selected depending on, for instance, the conditions of the affected site and subsequently fixing the substrate for feeding cells and/or tissues or the cell/tissue feeder to the damaged site by the suture of the substrate or feeder and the damaged site. Thereafter the guidance of a patient in conducting the desired movement of his joint will, if necessary, be carried out after the operation thereof.

[Industrial Applicability]

The present invention permits the production of various kinds of cell/tissue feeders, while making use of a porous body carrying a thin film surface and a porous surface. The use of this cell/tissue feeder in turn permits the firm fixation, through suture, thereof to a desired tissue-defective site; the reduction of any mechanical load possibly applied to the surface of the tissue defective site, and the use thereof further permits the extremely excellent tissue regeneration on the tissue-defective site, if preliminarily inoculating or seeding desired cells on the porous of the porous body to form a desired tissue. Therefore, the present invention can efficiently be used in the field in which cells are engineered, for instance, it can be used as a tissue and/or cell feeder for the transplantation of tissues and/or cells, as a tissue-forming scaffolding material for forming, in vitro, any desired tissue and as a substrate or carrier for the cultivation of cells, and further the present invention ultimately permits the effective use of such regenerated tissues in the field of the regenerative medical techniques.

[Brief Description of Symbols]

1a: Upper acrylic plate; 1b: lower acrylic plate; 2: spacer; 3: space; 21: thin film surface; 22: porous surface; 31: porous surface; 32: cartilage tissue; 51: patellar joint surface stained with H.E.; 52, 53: cartilage tissues stained with Collagen II; 61: cartilage portions stained with H.E. before and after the transplantation operation; 62: cartilage portions stained with toluidine blue before and after the transplantation operation; 63: cartilage tissues prior to the transplantation; 64: cartilage tissues after the transplantation.

The invention claimed is:

1. A substrate for feeding cells/tissues characterized in that it is composed of a unitary porous body comprising a silk protein and a physiologically active molecule selected from the group consisting of collagen, cell growth factors, and cell adhesion factors, wherein the substrate is obtained in a mold having a surface-roughened bottom or top surface and has a film surface having a tear strength of not less than 0.05 N as determined according to the Trouser Tear Method (JIS K7128) formed on a side of the surface of the mold free of any surface-roughening treatment and a porous surface having a pore size ranging from 50 to 500 μm formed on a side of the surface-roughened bottom or top surface of the mold.

2. A substrate for feeding cells/tissues comprising a unitary porous body comprising a silk protein and a physiologically active molecule selected from the group consisting of collagen, cell growth factors, and cell adhesion factors,
wherein the unitary porous body comprises a film surface having a tear strength of not less than 0.05 N as determined according to the Trouser Tear Method (JIS K7128) and a porous surface having a pore size ranging from 50 to 500 μm;
wherein the unitary porous body is obtained in a mold having a surface-roughened bottom or top surface;
wherein the film surface is formed on a side of the surface of the mold free of any surface-roughening treatment, and the porous surface is formed on a side of the surface-roughened bottom or top surface of the mold; and
wherein the unitary porous body is obtained by a method comprising
introducing an aqueous solution of the silk protein, to which a water-soluble organic solvent is added in an amount ranging from 0.05 to 10% by volume, into the mold;
freezing the aqueous solution over a predetermined time period; and
then thawing the frozen aqueous solution to thus form the unitary porous body.

3. A method for the production of a cell/tissue feeder characterized in that it comprises the steps of providing a unitary porous body as set forth in claim 2; seeding cells on the porous surface of the unitary porous body and cultivating the cells to thus form tissues.

4. The method for the production of a cell/tissue feeder as set forth in claim 3, wherein the cells are ones selected from the group consisting of cartilage cells, myeloid cells, peripheral mononuclear cells, myeloid mononuclear cells, somatic stem cells, and pluripotent cells.

5. The method for the production of a cell/tissue feeder as set forth in claim 3, wherein the tissues are ones selected from the group consisting of cartilage tissues, skin tissues, bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues.

6. The method for the production of a cell/tissue feeder as set forth in claim 3, wherein the cells are cartilage cells and the tissues are cartilage tissues.

7. A method for the regeneration of tissues characterized in that it comprises the steps of providing a unitary porous body as set forth in claim 2; seeding cells on the porous surface of the unitary porous body and cultivating the cells to thus form tissues.

8. The method for the regeneration of tissues as set forth in claim 7, wherein after the formation of the tissues, the resulting tissues are adapted to a tissue defective site.

9. The method for the regeneration of tissues as set forth in claim 7, wherein the cells are ones selected from the group consisting of cartilage cells, myeloid cells, peripheral mononuclear cells, myeloid mononuclear cells, somatic stem cells, and pluripotent cells.

10. The method for the regeneration of tissues as set forth in claim 7, wherein the tissues are ones selected from the group consisting of cartilage tissues, skin tissues, bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues.

11. The method for the regeneration of tissues as set forth in claim 7, wherein the cells are cartilage cells and the tissues are cartilage tissues.

12. A method for the production of a unitary porous body characterized in that it comprises the steps of introducing an aqueous solution of a silk protein, to which a water-soluble organic solvent is added in an amount ranging from 0.05 to 10% by volume, into a mold having a surface-roughened bottom or top surface; freezing the aqueous solution over a predetermined time period; and then thawing the frozen aqueous solution to thus form a unitary porous body comprising the silk protein and having a thin film surface formed on a side of the surface of the mold free of any surface-roughening treatment and a porous surface formed on a side of the surface-roughened bottom and top surface of the mold.

13. The method for the production of a unitary porous body as set forth in claim 12, wherein the surface-roughened surface of the unitary porous body is one formed by adhering filter paper, a nonwoven fabric, or a surface-roughened film onto the mold surface, or one formed by mechanically or chemically treating the surface of the mold.

14. The substrate for feeding cells/tissues as set forth in claim 1, wherein the surface-roughened surface of the unitary porous body has a surface shape of filter paper, a nonwoven fabric, or a surface-roughened film adhered onto the mold surface, or a mechanically or chemically treated surface shape or profile of the mold.

15. A substrate for feeding cells/tissues characterized in that it is composed of a unitary porous body comprising a silk protein and a physiologically active molecule selected from the group consisting of collagen, cell growth factors, and cell adhesion factors, wherein the substrate is obtained in a mold having a surface-roughened bottom or top surface and comprising a film surface having a tear strength of not less than 0.05 N as determined according to the Trouser Tear Method (JIS K7128) and a porous surface having a pore size ranging from 50 to 500 μm.

16. The method for the regeneration of tissues as set forth in claim 8, wherein the cells are ones selected from the group consisting of cartilage cells, myeloid cells, peripheral mononuclear cells, myeloid mononuclear cells, somatic stem cells, and pluripotent cells.

17. The method for the regeneration of tissues as set forth in claim 8, wherein the tissues are ones selected from the group consisting of cartilage tissues, skin tissues, bone tissues, muscular tissues, fascial tissues, periosteal tissues, adipose tissues, mucosal tissues, serosal tissues, tendon tissues, peritendinous tissues, corneal tissues, tympanic tissues,' vascular adventitial tissues, nerve tissues, periodontal tissues, myocardial tissues, and hepatic tissues.

18. A method for fixing a cell/tissue feeder on an affected site of a patient characterized in that it comprises the steps of providing the unitary porous body having a thin film surface and a porous surface as set forth in claim 1; seeding cells on the porous surface of the unitary porous body; cultivating the cells to thus form cells/tissues feeder carrying the corresponding tissues formed thereon; and fixing the resulting cell/tissue feeder, by suturing the same through the thin film surface of the feeder, to the affected site.

19. The method for fixing a cell/tissue feeder on an affected site of a patient as set forth in claim 18, wherein the unitary porous body comprises a silk protein obtained in a mold having a surface-roughened bottom or top surface and having a thin film surface formed on a side of the surface of the mold free of any surface-roughening treatment and a porous surface formed on a side of the surface-roughened bottom and top surface of the mold.

20. The method for fixing a cell/tissue feeder on an affected site of a patient as set forth in claim 18, wherein the cells are ones selected from the group consisting of cartilage cells, myeloid cells, peripheral mononuclear cells, myeloid mononuclear cells, somatic stem cells, and pluripotent cells.

21. The method for fixing a cell/tissue feeder on an affected site of a patient as set forth in claim 18, wherein the tissues are ones selected from the group consisting of cartilage tissues, skin tissues, bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues.

22. A method for treating an affected site of a patient characterized in that it comprises the steps of providing the unitary porous body having a thin film surface and a porous surface as set forth in claim 1; seeding cells on the porous surface of the unitary porous body; cultivating the cells to thus form cells/tissues feeder carrying the corresponding tissues formed thereon; and fixing the resulting cell/tissue feeder, by suturing the same through the thin film surface of the feeder, to the affected site, thereby the affected site is treated.

23. A method for treating an affected site of a patient characterized in that it comprises the steps of providing the unitary porous body having a thin film surface and a porous surface as set forth in claim 14; seeding cells on the porous surface of the unitary porous body; cultivating the cells to thus form cells/tissues feeder carrying the corresponding tissues formed thereon; and fixing the resulting cell/tissue feeder, by suturing the same through the thin film surface of the feeder, to the affected site, thereby the affected site is treated.

24. A method for treating an affected site of a patient characterized in that it comprises the steps of providing the unitary porous body having a thin film surface and a porous surface as set forth in claim 15; seeding cells on the porous surface of the unitary porous body; cultivating the cells to thus form cells/tissues feeder carrying the corresponding tissues formed thereon; and fixing the resulting cell/tissue feeder, by suturing the same through the thin film surface of the feeder, to the affected site, thereby the affected site is treated.

25. The method for treating an affected site of a patient as set forth in claim 22, wherein the unitary porous body comprises a silk protein obtained in a mold having a surface-roughened bottom or top surface and having a thin film surface formed on a side of the surface of the mold free of any surface-roughening treatment and a porous surface formed on a side of the surface roughened bottom and top surface of the mold.

26. The method for treating an affected site of a patient as set forth in claim 22, wherein the cells are ones selected from the group consisting of cartilage cells, myeloid cells, peripheral mononuclear cells, myeloid mononuclear cells, somatic stem cells, and pluripotent cells.

27. The method for treating an affected site of a patient as set forth in claim 22, wherein the tissues are ones selected from the group consisting of cartilage tissues, skin tissues, bone tissues, muscular tissues, fascial tissues, periosteal tissues, adipose tissues, mucosal tissues, serosal tissues, tendon tissues, peritendinous tissues, corneal tissues, tympanic tissues, vascular adventitial tissues, nerve tissues, periodontal tissues, myocardial tissues, and hepatic tissues.

28. The substrate for feeding cells/tissues as set forth in claim 2, wherein the surface-roughened surface of the unitary porous body has such a surface shape that a surface shape of filter paper, a nonwoven fabric, a surface-roughened film adhered onto the mold surface, or a surface shape or profile formed by mechanically or chemically treating surface of the mold is transferred.

* * * * *